(12) United States Patent
Diederich et al.

(10) Patent No.: US 8,025,688 B2
(45) Date of Patent: *Sep. 27, 2011

(54) APPARATUS FOR THERMAL THERAPY OF PROSTATE GLAND WITH ULTRASOUND ENERGY

(75) Inventors: Chris J. Diederich, Novato, CA (US); Everette C. Burdette, Champaign, IL (US)

(73) Assignees: The Regents of the University of California, Oakland, CA (US); Dorner Medical Systems, Inc., Kennesaw, GA (US)

( * ) Notice: Subject to any disclaimer, the term of this patent is extended or adjusted under 35 U.S.C. 154(b) by 2469 days.

This patent is subject to a terminal disclaimer.

(21) Appl. No.: 10/397,070

(22) Filed: Mar. 24, 2003

(65) Prior Publication Data

US 2004/0044375 A1 Mar. 4, 2004

Related U.S. Application Data

(63) Continuation of application No. 08/858,912, filed on May 19, 1997, now Pat. No. 6,537,306, which is a continuation of application No. 08/332,997, filed on Nov. 1, 1994, now Pat. No. 5,733,315, which is a continuation-in-part of application No. 08/291,336, filed on Aug. 17, 1994, now abandoned, which is a continuation-in-part of application No. 08/083,967, filed on Jun. 25, 1993, now Pat. No. 5,391,197, which is a continuation-in-part of application No. 07/976,232, filed on Nov. 13, 1992, now abandoned.

(51) Int. Cl.
*A61F 7/00* (2006.01)

(52) U.S. Cl. ............ 607/96; 607/113; 607/143; 604/22; 601/2; 600/439

(58) Field of Classification Search .................... 607/96, 607/101–105, 113, 138, 143; 600/437, 439; 604/22; 601/2
See application file for complete search history.

(56) References Cited

U.S. PATENT DOCUMENTS 3,977,408 A 8/1976 MacKew
(Continued)

FOREIGN PATENT DOCUMENTS

DE 28 16 391 A1 11/1978
(Continued)

OTHER PUBLICATIONS

Hynynen et al.; "Small Cylindrical Ultrasound Sources for Induction of Hyperthermia Via Body Cavities or Interstitial Implants," Int. J. Hyperthermia, vol. 9, No. 2, pp. 263-274, (1993).

(Continued)

*Primary Examiner* — Ahmed Farah
(74) *Attorney, Agent, or Firm* — John P. O'Banion

(57) ABSTRACT

An apparatus for applying thermal energy to a prostate gland, comprising a support tube having a longitudinal passageway, a power lead channeled through the longitudinal central passageway and an ultrasound crystal disposed around at least part of the support tube. The ultrasound crystal is coupled to the power lead which provides the power to energize the ultrasound crystal and generate ultrasound energy providing thermal therapy to the prostate gland. The ultrasound crystal further includes inactivated portions for reducing ultrasound energy directed to the rectal wall of the patient. A sealant is disposed in contact with the ultrasound crystal allowing vibration necessary for efficient ultrasound energy radiation for the thermal therapy of the prostate gland.

25 Claims, 14 Drawing Sheets

U.S. PATENT DOCUMENTS

| | | | |
|---|---|---|---|
| 4,311,154 A | 1/1982 | Sterzer et al. | |
| 4,312,364 A | 1/1982 | Convert et al. | |
| 4,378,806 A | 4/1983 | Henley-Cohn | |
| 4,462,408 A | 7/1984 | Silverstein et al. | |
| 4,586,512 A | 5/1986 | Do-huu et al. | |
| 4,601,296 A | 7/1986 | Yerushalmi | |
| 4,612,940 A | 9/1986 | Kasevich et al. | |
| 4,662,383 A | 5/1987 | Sogawa et al. | |
| 4,671,293 A | 6/1987 | Shaulov | |
| 4,681,122 A | 7/1987 | Winters et al. | |
| 4,800,899 A | 1/1989 | Elliott | |
| 4,813,429 A | 3/1989 | Eshel et al. | |
| 4,907,589 A | 3/1990 | Cosman | |
| 4,955,377 A | 9/1990 | Lennox et al. | |
| 4,961,435 A | 10/1990 | Kitagawa et al. | |
| 4,967,765 A | 11/1990 | Turner et al. | |
| 4,977,902 A | 12/1990 | Sekino et al. | |
| 5,002,058 A | 3/1991 | Martinelli | |
| 5,007,437 A | 4/1991 | Sterzer | |
| 5,025,778 A | 6/1991 | Silverstein et al. | |
| 5,070,879 A | 12/1991 | Herres | |
| RE33,791 E | 1/1992 | Carr | |
| 5,090,414 A | 2/1992 | Takano | |
| 5,158,536 A | 10/1992 | Sekins et al. | |
| 5,167,231 A | 12/1992 | Matsui | |
| 5,207,672 A * | 5/1993 | Roth et al. | 606/10 |
| 5,271,408 A | 12/1993 | Breyer et al. | |
| 5,304,214 A * | 4/1994 | DeFord et al. | 607/105 |
| 5,344,435 A | 9/1994 | Turner et al. | |
| 5,351,691 A | 10/1994 | Brommersma | |
| 5,385,544 A * | 1/1995 | Edwards et al. | 604/22 |
| 5,391,197 A * | 2/1995 | Burdette et al. | 601/3 |
| 5,526,815 A | 6/1996 | Granz et al. | |
| 5,620,479 A | 4/1997 | Diederich | |
| 5,733,315 A * | 3/1998 | Burdette et al. | 601/97 |
| 5,865,801 A | 2/1999 | Houser | |
| 5,902,308 A | 5/1999 | Murphy | |
| 6,179,858 B1 | 1/2001 | Squire et al. | |
| 6,599,288 B2 | 7/2003 | Maguire | |
| 6,607,502 B1 | 8/2003 | Maguire | |

FOREIGN PATENT DOCUMENTS

| | | |
|---|---|---|
| DE | 24 07 599 C3 | 1/1982 |
| DE | 37 19 705 | 12/1987 |
| EP | 0 370 890 A1 | 11/1989 |
| EP | 468-847 | 1/1992 |
| GB | 2 045 620 A | 3/1980 |
| RU | 1266548 | 10/1986 |
| RU | 1528509 | 12/1989 |
| RU | 1648504 | 5/1991 |
| WO | WO 85/02779 | 7/1985 |
| WO | WO 93/16641 | 9/1993 |

OTHER PUBLICATIONS

Kaplan, Steven A. et al.; "Prostatic and Periprostatic Interstital Temperature Measuremetns in Patients Treated With Transretal Thermal Therapy (Local Intracavitary Microwave Hyperthermia)," The Journal of Urology, vol. 147, pp. 1562-1565, (Jun. 1992).

Kapp, Daniel S. et al.; "Parameters Predictive for Complications of Treatment With Combined Hyperthermia and Radiation Therapy," Int. J. of Radiation Oncology, Biology, Physics, vol. 22, No. 5, pp. 999-1008, (1988).

Sapozink, M.D..et al.; "Introduction to Hyperthermia Device Evaluation," Int. J. of Hyperthermia, vol. 4, No. 1, pp. 1-15, (1988).

Kapp, Daniel S. et al.; "Stanford University Institutional Report, Phase I Evaluation of Equipment for Hyperthermia Treatment of Cancer," Int. J. Hyperthermia, vol. 4, No. 1, pp. 75-115, (1988).

Shimm, David S. et al.; "Clinical Evaluation of Hyperthermia Equipment: the University of Arizona Institutional Report for the NCI Hyperthermia Equipment Evaluation Contract," Int. J. Hyperthermia, vol. 4, No. 1, pp. 39-51, (1988).

Petrowicz, Otto et al.; "High-Frequency Transmitter for the Localized Heat Treatment of the Prostate Gland," National Cancer Institute Monograph No. 61, pp. 473-476, (1982).

Harada, et al.; "Microwave Surgical Treatment of Diseases of Prostate," Urology, vol. XXVI, No. 6, (Dec. 1985).

Ding-Jui Li, M.D. et al.; "Design and Thermomety of an Intracavitary Microwave Applicator Suitable for Treatment of Some Vaginal and Rectal Cancers," Int. J. Radiation Oncology Biol. Phys., vol. 10, No. 11, pp. 2155-2162, (Nov. 1984).

Steffer, C. et al. (eds.); "Cancer Therapy by Hyperthermia and Radiation," Proceedings of the 2nd International Symposium, Essen, (Jun. 2-4, 1977).

Mendecki, J. et al.; "Induction of Hyperthermia in Deep-Seated Tumors by a Special Microwave Applicator," Proceedings of the 2nd International Symposium, Essen, (Jun. 2-4, 1977).

LeBourgeois et al.; "An Interstitial Device for Microwave Hyperthermia of Human Tumors," Proceedings of the 2nd International Symposium, Essen, (Jun. 2-4, 1977).

Hynynen; "The Feasibility of Interstitial Ultrasound Hyperthermia," Am. Assoc. Phys. Med. J. (Jul./Aug. 1992).

Diederich, C.J., et al.; "Ultrasound Technology for Interstitial Hyperthermia," Medical Radiology Interstitial and Intracavitary Thermoradiotherapy, Springer-Verlag, (1993).

Diederich, C.J.; "A Design Study of Ultrasound Applicators for Interstitial Hyperthermia," NAH Annual Meeting, (1993).

Diederich, C.J.; "A Theoretical-Study of Ultrasound Interstitial Hyperthermia," Medical Physics, vol. 19, No. 3, (May/Jun. 1992).

Diederich, C.J.; "The Design of Ultrasound Applicators for Interstitial Hyperthermia," IEEE Ultrasonic Symposium, (Nov. 1993).

Lancaster, C., "Interstitial Microwave Thermoablation For Localized Prostate Cancer", Urology 53 (4), 1999, pp. 828-831. [1 p. abstract].

* cited by examiner

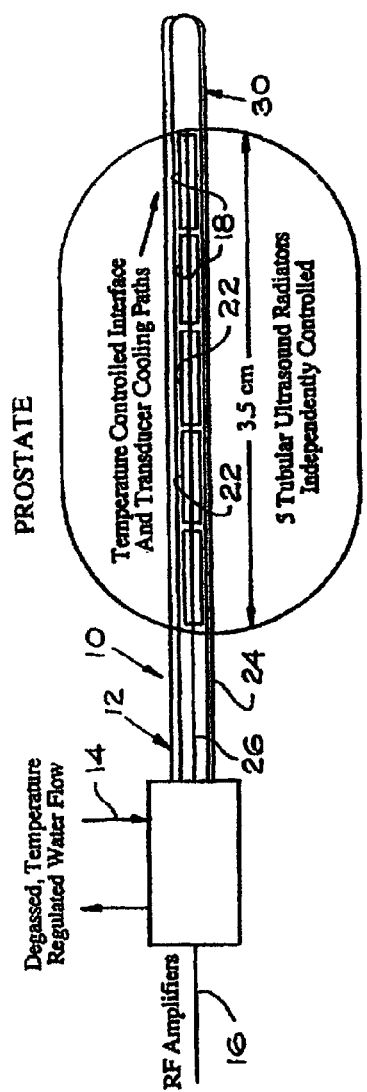
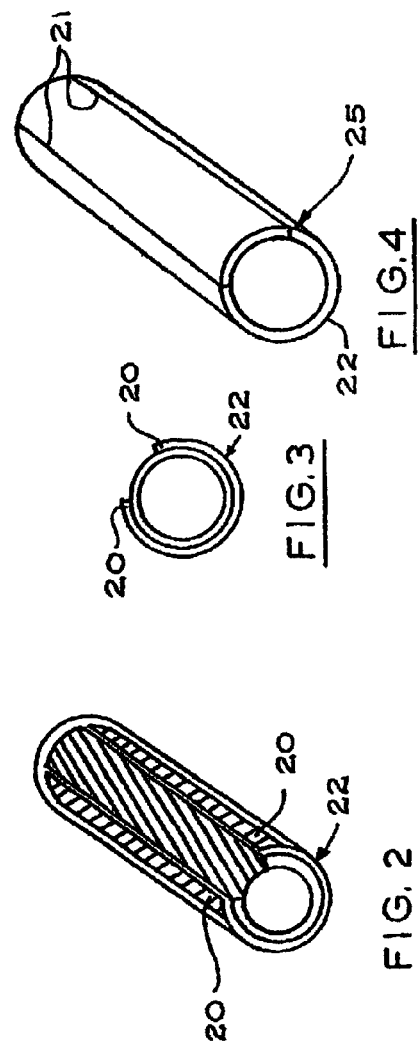

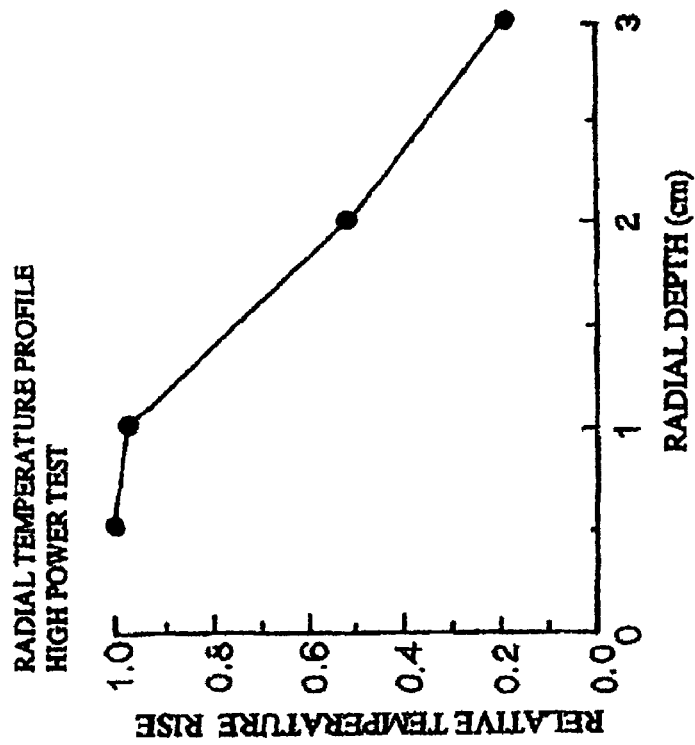
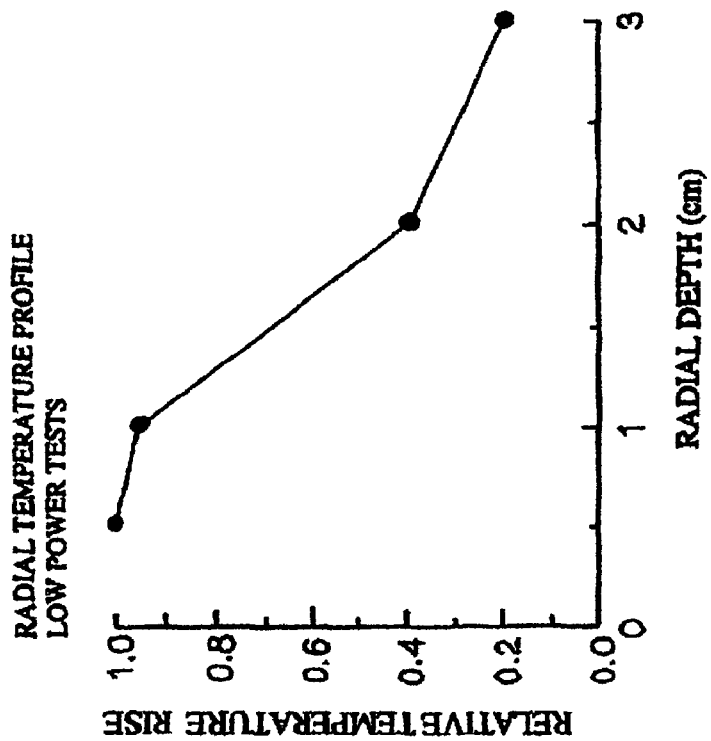

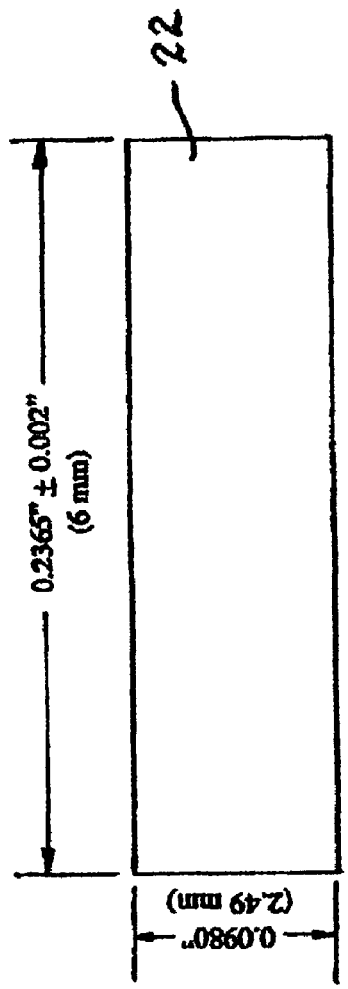
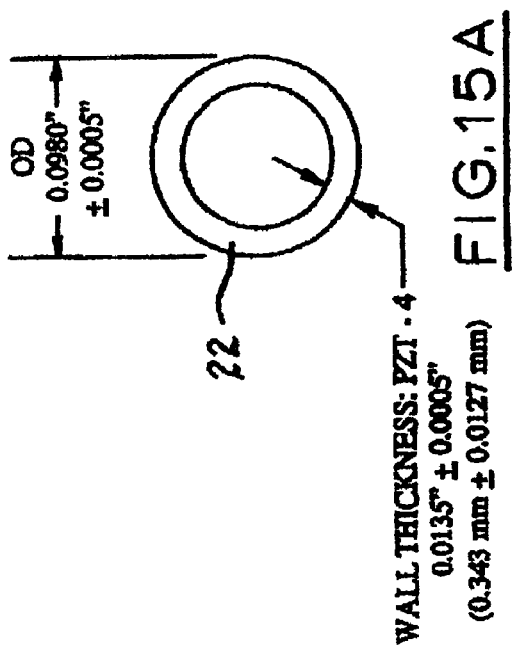
FIG.15B
FIG.15A

APPARATUS FOR THERMAL THERAPY OF PROSTATE GLAND WITH ULTRASOUND ENERGY

CROSS-REFERENCE TO RELATED APPLICATIONS

The present application is a continuation of U.S. patent application Ser. No. 08/858,912 filed on May 19, 1997, now U.S. Pat. No. 6,537,306, which is a continuation of U.S. patent application Ser. No. 08/332,997 filed on Nov. 1, 1994, now U.S. Pat. No. 5,733,315, which is a continuation-in-part of U.S. patent application Ser. No. 08/291,336 filed on Aug. 17, 1994, now abandoned which is a continuation-in-part of U.S. patent application Ser. No. 08/083,967, filed Jun. 25, 1993, now U.S. Pat. No. 5,391,197, which is a continuation-in-part of U.S. patent application Ser. No. 07/976,232 filed on Nov. 13, 1992, now abandoned in favor of U.S. patent application Ser. No. 08/291,336, now abandoned. The aforementioned U.S. patent application Ser. Nos. 08/858,912 and 08/332,997 are herein incorporated in their entirety by reference thereto. The Detailed Description of the Preferred Embodiment of the aforementioned U.S. patent application Ser. No. 08/083,967 is incorporated herein for additional details regarding example delivery systems and ultrasound energy deposition techniques.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to an apparatus and method for performing a thermotherapy patient treatment protocol. More particularly, the invention relates to a novel apparatus and method for heating the prostate gland for therapeutic purposes.

2. Description of Related Art

Thermotherapy treatment is a relatively new method of treating diseased and/or undesirably enlarged human prostate tissues. Hyperthermia treatment is well known in the art, involving the maintaining of a temperature between about 41.5° through 45° C. Thermotherapy, on the other hand, usually requires energy application to achieve a temperature above 45° C. for the purposes of coagulating the target tissue. Tissue coagulation beneficially changes the density of the tissue. As the tissue shrinks, forms scars and is reabsorbed, the impingement of the enlarged tissues, such as an abnormal prostate, is substantially lessened.

The higher temperatures required by thermotherapy require delivery of larger amounts of energy to the target prostate tissues. At the same time, it is important to shield nontarget tissues from the high thermotherapy temperatures used in the treatment. Providing safe and effective thermotherapy, therefore, requires devices which have further capabilities compared to those which are suitable for hyperthermia.

Though devices and methods for treating benign prostatic hyperplasia have evolved dramatically in recent years, significant improvements have not occurred and such progress is badly needed. As recently as 1983, medical textbooks recommended surgery for removing impinging prostatic tissues and four different surgical techniques were utilized. Suprapubic prostatectomy was a recommended method of removing the prostate tissue through an abdominal would. Significant blood loss and the concomitant hazards of any major surgical procedure were possible with this approach.

Perineal prostatectomy was an alternatively recommended surgical procedure which involved gland removal through an incision n the perineum. Infection, incontinence, impotence or rectal injury were more likely with this method than with alternative surgical procedures.

Transurethral resection of the prostate gland has been another recommended method of treating benign prostatic hyperplasia. This method required inserting a rigid tube into the urethra. A loop of wire connected with electrical current was rotated in the tube to remove shavings of the prostate at the bladder orifice. In this way, no incision was needed. However, strictures were more frequent and repeat operations were sometimes necessary.

The other recommended surgical technique for treatment of benign prostatic hyperplasia was retropubic prostatectomy. This required a lower abdominal incision through which the prostate gland was removed. Blood loss was more easily controlled with this method, but inflammation of the pubic bone was more likely.

With the above surgical techniques, the medical textbooks noted the vascularity of the hyperplastic prostate gland and the corresponding dangers of substantial blood loss and shock. Careful medical attention was necessary following these medical procedures.

The problems previously described led medical researchers to develop alternative methods for treating benign pro static hyperplasia. Researchers began to incorporate heat sources in. Foley catheters after discovering that enlarged mammalian tissues responded favorably to increased temperatures. Examples of devices directed to treatment of prostate tissue include U.S. Pat. No. 4,662,383 (Harada). U.S. Pat. No. 4,967,765 (Turner), U.S. Pat. No. 4,662,383 (Sogawa) and German Patent No. DE 2407559 C3 (Dreyer). Though these references disclosed structure which embodied improvements over the surgical techniques, significant problems still remained unsolved. Recent research has indicated that enlarged prostate glands are most effectively treated with higher temperatures than previously thought. Complete utilization of this discovery has been tempered by difficulties in shielding rectal wall tissues and other nontarget tissues. While shielding has been addressed in some hyperthermia prior art devices, the higher energy field intensities associated with thermotherapy necessitate structures having further capabilities beyond those suitable for hyperthermia. For example, the symmetrical microwave-based devices disclosed in the above-referenced patents have generally produced relatively uniform cylindrical energy fields. Even at the lower energy field intensities encountered in hyperthermia treatment, unacceptably high rectal wall temperatures have limited treatment periods and effectiveness. Further while shielding using radioreflective fluids has been disclosed in the prior art (see for example European Patent Application No. 89,403,199) the location of such radioreflective fluid appears to increase energy field intensity at the bladder and rectal wall. This is contrary to one of the objects of the present invention.

In addition, efficient and selective cooling of the devices is rarely provided. This increases patient discomfort and increases the likelihood of healthy tissue damage. These problems have necessitated complex and expensive temperature monitoring systems along the urethral wall.

Finally, the symmetrical designs of the above-referenced devices do not allow matching of the energy field to the shape of the abnormally enlarged prostate gland. Ideally, the energy field reaching the tissues should be asymmetric and generally should expose the upper and lateral (side) impinging lobes of the prostate gland to the highest energy. In addition, the field is ideally substantially elliptical such that the energy reaching the sphincters is minimized.

BRIEF SUMMARY OF THE INVENTION

It is therefore an object of the invention to provide an improved apparatus and method suitable for ultrasound treatment of tissue.

It is a further object of the invention to provide an improved apparatus and method for thermotherapy treatment which provides a smaller probe with higher ultrasound energy output on target tissues.

It is yet a further object of the invention to provide a novel method and apparatus having high ultrasound energy output on target tissues while producing substantially no energy output directed to nontarget tissues.

It is yet another object of the invention to provide an improved applicator designed to be inserted into an orifice of a male patient, wherein the applicator includes a small diameter ultrasound probe.

It is a still further object of the invention to provide a novel means for dynamic monitoring of the treatment temperature distribution and to use such information to aid in the control of the deposited power level and its distribution.

It is another object of the invention to provide and improved ultrasonic applicator which can be inserted into the urethra and can be positioned with respect to the prostate and maintained in position during treatment.

It is a further object of the invention to provide an improved method and apparatus using ultrasound energy for the treatment of prostate disease and, more particularly to provide an ultrasound applicator consisting of multiple transducers which can be inserted into the urethra or rectum and direct the energy in such a manner as to selectively treat the prostate gland.

It is yet another object of the invention to provide a novel method and apparatus utilizing ultrasound energy to achieve therapeutic temperatures in the prostate with better control of power deposition spatially within the prostate gland than is possible with prior art devices.

It is an additional object of the invention to provide an array of ultrasound transducers producing an energy field having a gap or "dead zone" whereby tissues (such as the rectum, the distal sphincter and the verumontanum) are protected from energy transmission.

It is a further object of the invention to provide improved control of both the ultrasonic power level and the distribution of the power deposited in the prostate in a dynamic fashion which compensates for physiological changes (temperature, blood flow effects) that can occur during therapy and accommodates operator-desired alterations in the therapeutic energy distribution within the prostate It is another object of the invention to provide an improved thermotherapy device which includes a collimated irradiation of a target zone generally and selective cooling of nontarget tissues.

It is still an additional object of the invention to provide an improved thermotherapy device which reduces tissue damage and discomfort by providing more effective cooling to non-target tissues.

It is an additional object of the invention to provide an improved thermotherapy apparatus having one or more extended, and nondistensible but expandable balloons.

It is an additional object of the invention to provide an improved thermotherapy device which includes ultrasound transducers or other energy sources capable of producing a substantially asymmetric energy output field, thus minimizing energy reaching the rectal wall in benign prostatic hyperplasia thermotherapy treatment.

It is still a further object of the invention to provide an improved thermotherapy apparatus which produces an energy field shaped in accordance with the enlarged mammalian gland to be treated.

Other advantages and features of the invention, together with the organization and manner of operation thereof, will become apparent from the following detailed description when taken in conjunction with the accompanying drawings, wherein like elements have like numerals throughout the drawings.

BRIEF DESCRIPTION OF THE SEVERAL VIEWS OF THE DRAWING(S)

FIG. 1 illustrates a schematic view of a thermotherapy device constructed in accordance with one form of the invention;

FIG. 2 shows an isometric view of an ultrasound crystal having a portion of its electrode coating removed;

FIG. 3 illustrates an end view of the ultrasound crystal constructed in accordance with the invention and shown in FIG. 2;

FIG. 4 shows an isometric view of an ultrasound crystal including two score lines creating a region rendered incapable of radiating ultrasound energy;

Figure 10:
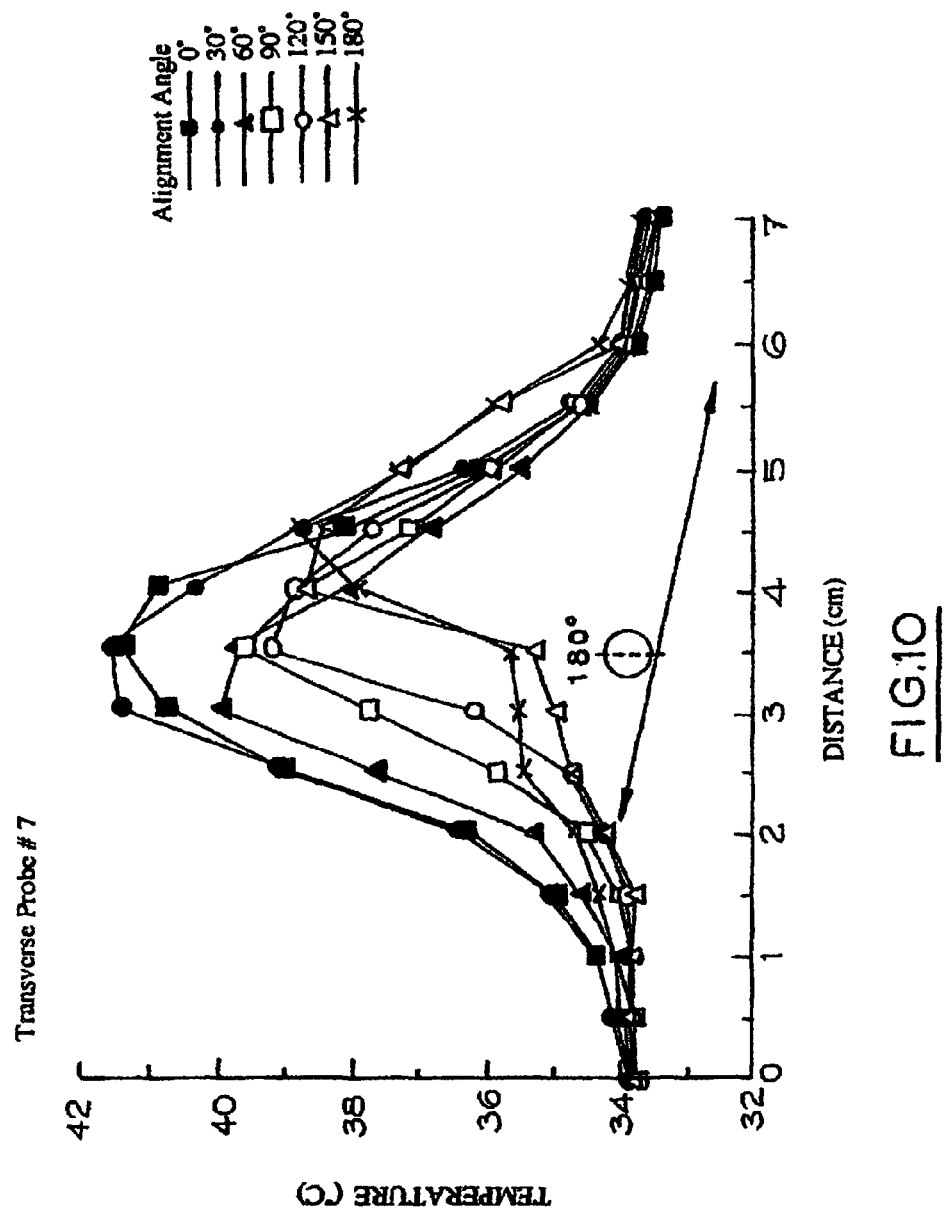
Figure 11:
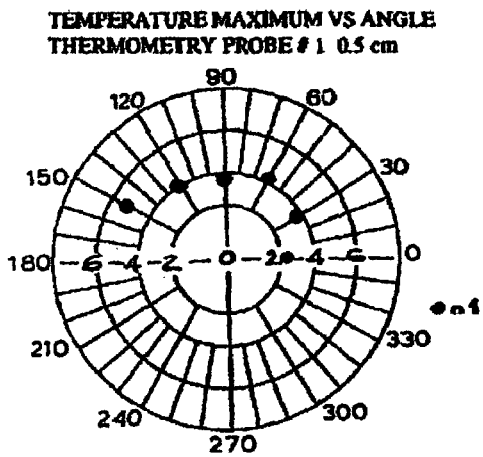
Figure 11:
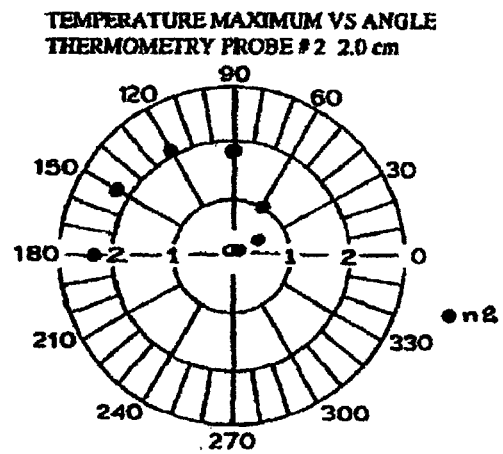
Figure 11:
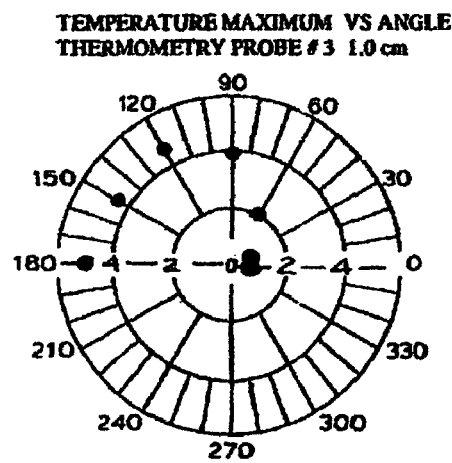
Figure 11:
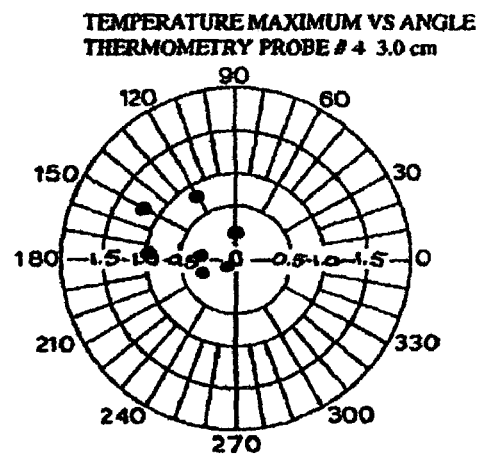
Figure 11:
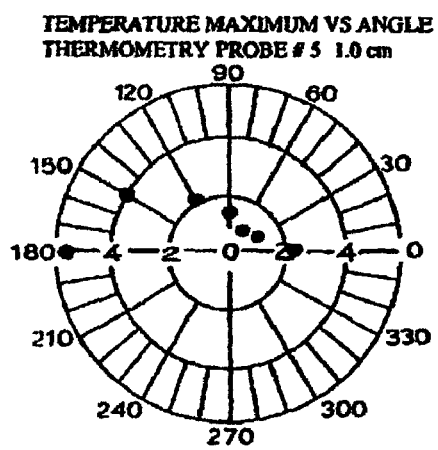
Figure 12B:
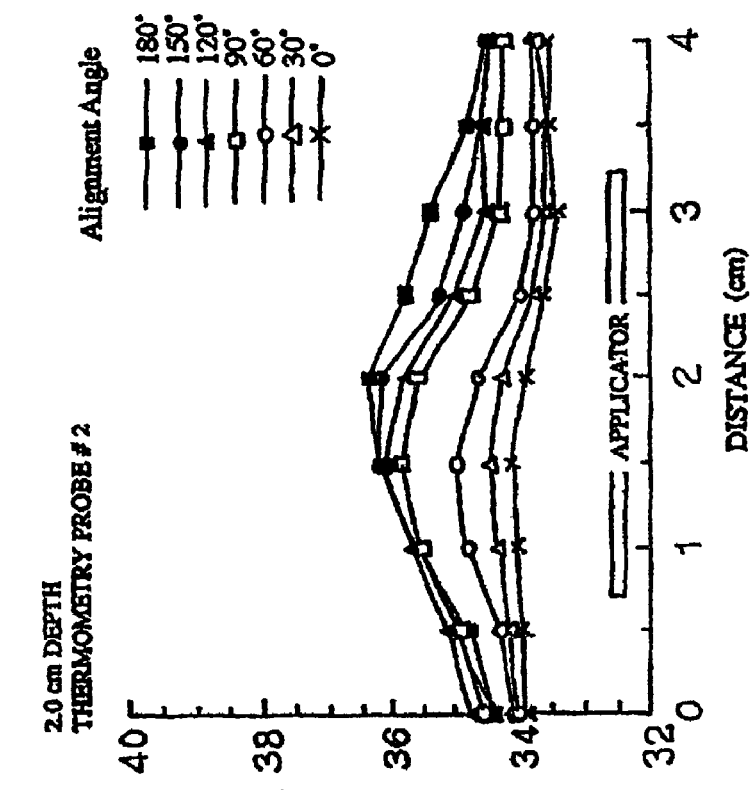
Figure 12A:
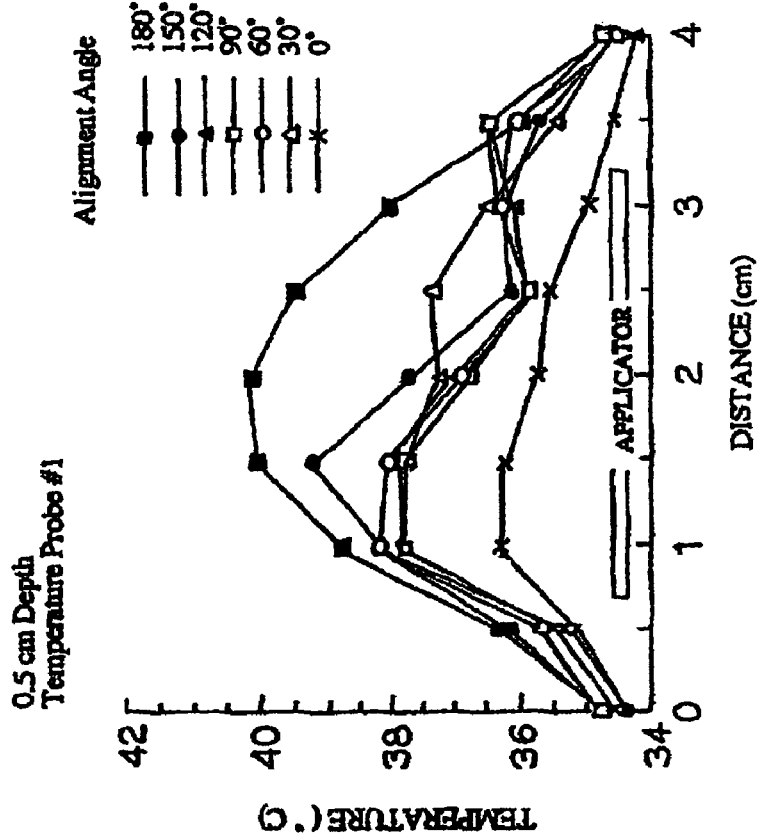
Figure 12D:
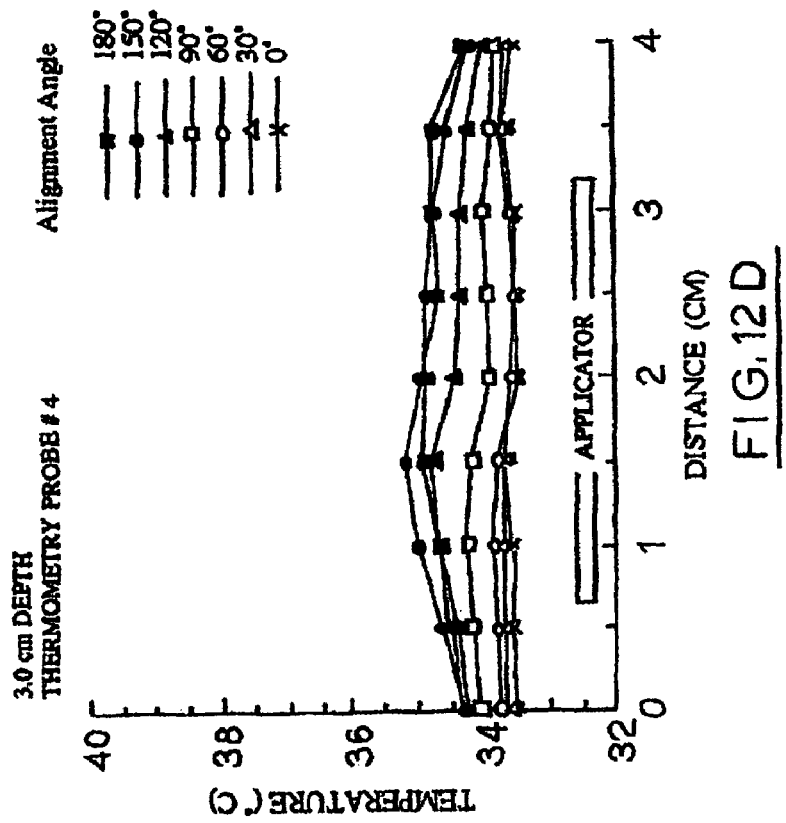
Figure 12C:
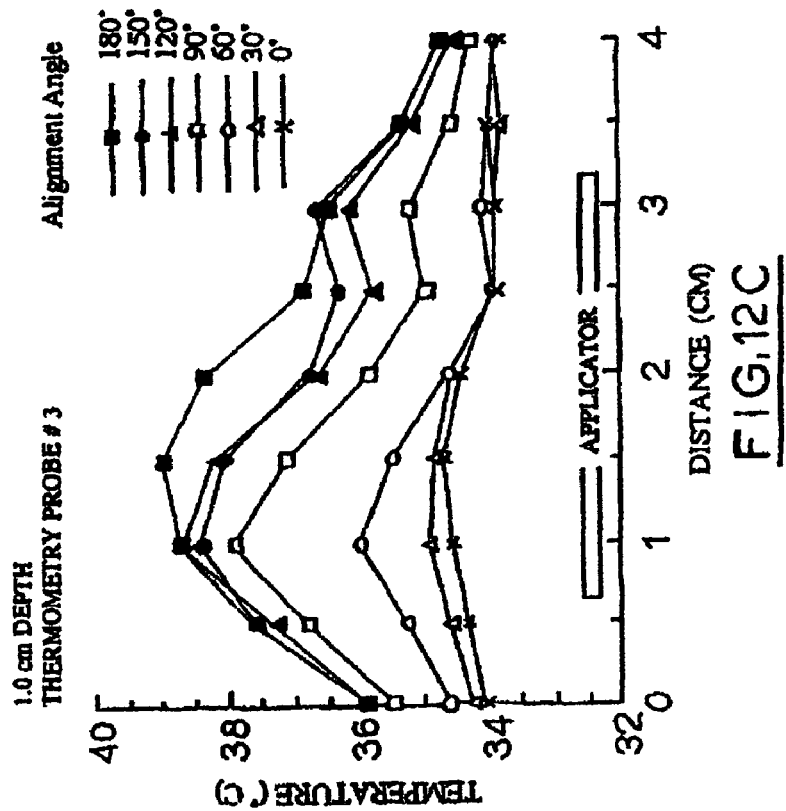
Figure 12E:
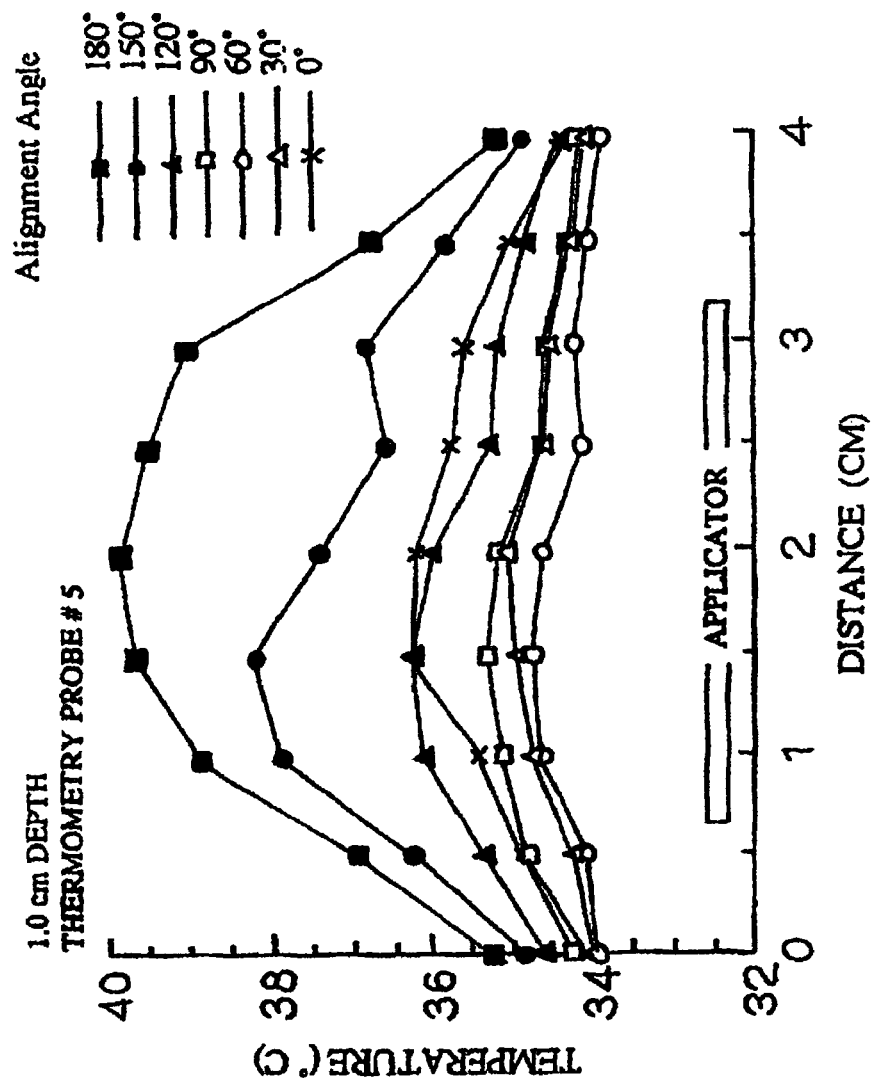
Figure 13B:
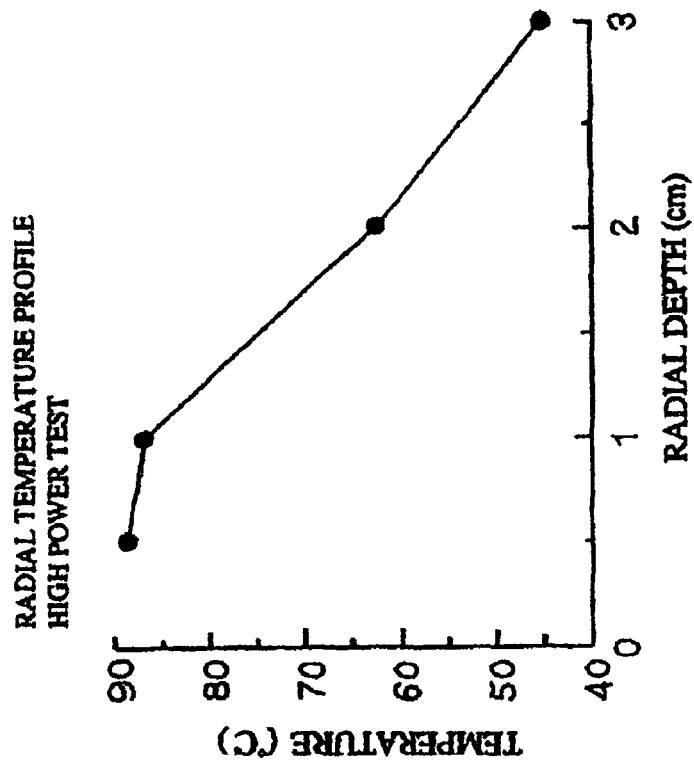
Figure 13A:
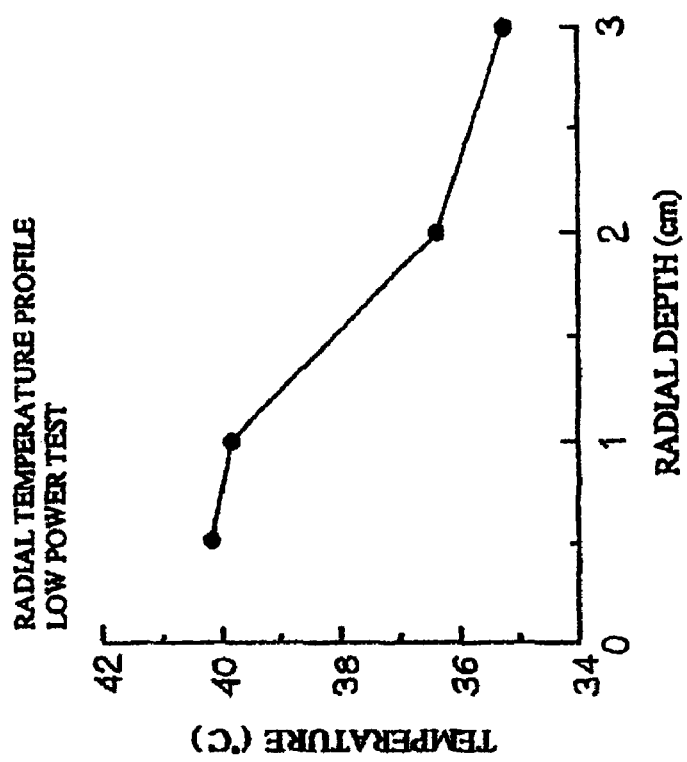
Figure 14:
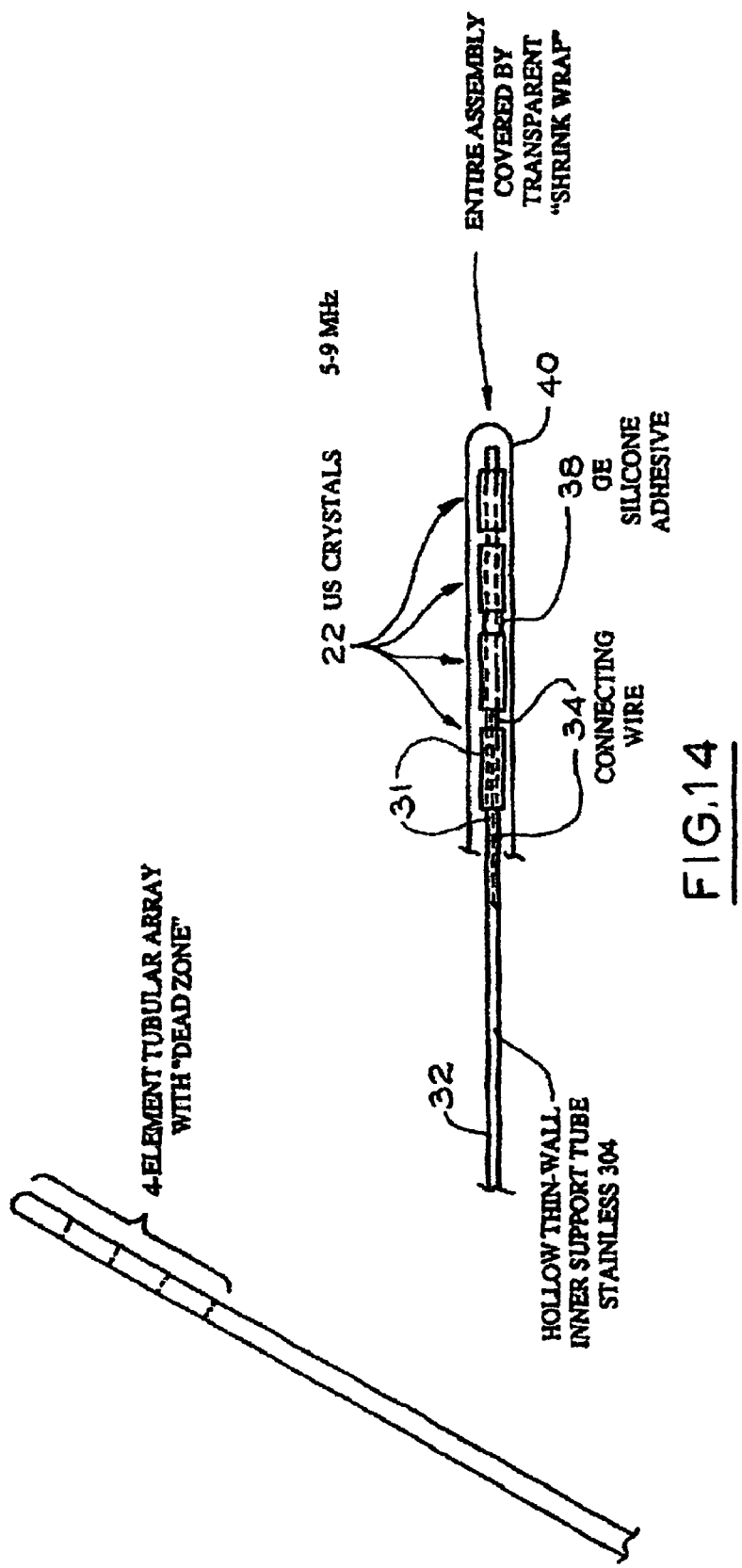

FIGS. 9A-9D show longitudinal temperature profiles measured in pig thigh muscle at A) 0.5 cm; B) 1 cm; C) 2.0 cm; and D) 3.0 cm radial depths;

FIG. 10 illustrates tangential temperature profiles measured in the pig thigh muscle across the central heating zone;

FIGS. 11A-11E illustrate angular temperature profiles at a) Probe #1, 0.5 cm depth; b) Probe #2, 2 cm depth; c) Probe #3, 1.0 cm; d) Probe #4, 3.0 cm and e) Probe #5, 1.0 cm;

FIGS. 12A-12E show a different plot format of angular temperature at a) Probe #1, 0.5 cm depth; b) Probe #2, 2 cm depth; c) Probe #3, 1.0 cm; d) Probe #4, 3.0 cm and e) Probe #5, 1.0 cm;

FIGS. 13A-13D illustrate radial temperature profiles in the pig thigh muscle after ten minutes of therapy for low power tests (FIGS. 13A and 13C) and high power tests (FIGS. 13B and 13D);

FIG. 14 shows a front view of an ultrasound applicator constructed in accordance with one form of the invention;

FIG. 15A illustrates an end view of an ultrasound crystal useful in one form of the intervention; and FIG. 15B shows a front view of the crystal shown in FIG. 15A.

DETAILED DESCRIPTION OF THE INVENTION

Referring now to the figures and more particularly to FIG. 1, a thermotherapy device constructed in accordance with the invention is indicated generally at 10. Throughout the application when referring to "thermotherapy," this terminology shall be meant to include both thermotherapy treatment as well as hyperthermia treatment unless specifically stated to exclude one therapy.

The thermotherapy device includes a delivery system 12 which is coupled to the degassed and temperature regulated water flow 14 as well as RF amplifiers 16 and more fully described in U.S. patent application Ser. No. 08/083,967. While five tubular ultrasound transducers 18 are shown for non-limiting, illustrative purposes, it will be apparent to one skilled in the art that the number and configuration of ultrasound transducers can be varied depending on the particular application involved.

The delivery system can take a number of forms, though preferably a delivery system such as the one described in U.S. patent application Ser. No. 07/976,232 is used. The critical parameters of the delivery system 12 include the ability to provide degassed and temperature related water flow into the delivery system adjacent prostate tissue to be treated, as well as enabling individual control of each of the ultrasound transducers 18.

The ultrasound transducers 18 are preferably substantially cylindrical in shape. Conventional transducers 18 having this shape radiate a substantially symmetrical energy field. This has been found to be undesirable in prostate treatment as explained in detail in U.S. patent application Ser. No. 08/083, 967. As described therein, the primary problem with a symmetrical energy field is heating of the rectal wall during prostate treatment. Irreversible damage to the rectal wall can result from such an energy field if power levels are sufficient to effectively treat areas of the prostate. Accordingly, the ultrasound transducers 18 are modified in accordance with one form of the invention.

The ultrasound transducers 18 are modified to create a portion incapable of producing virtually any ultrasound energy. This can be accomplished in one of two ways in accordance with this form of the invention. The first method (as shown in FIGS. 2 and 3) involves removing the electrode coating 20 from a portion of the ultrasound crystal 22. As used herein, the term "ultrasound crystal" shall refer to the nickel-plated piezo ceramic structure which is unconnected to a housing 24, power leads 26 or the RF amplifiers 16. The term "ultrasound transducer; shall refer to the ultrasound crystal 22 coupled to power leads 26 and mounted on a housing 24. Removing part of the electrode coating 20 as shown in FIGS. 2 and 3 provides a means for protecting the rectal wall of the patent from undesirably heating by shaping the energy field. This enables energy levels, and therefore the heating temperatures of the prostate, to be increased for more effective thermal therapy.

An alternative way of producing a portion which is substantially incapable of producing ultrasound energy is to score the electrode portion 21 of the ultrasound crystal 22. While the depth of score lines 25 can be varied, preferably the scoring extends to a depth of 40-50% of the depth of the ultrasound crystal 22 exterior. The scoring can be accomplished using conventional cutting tools such as a diamond saw.

While a variety of ultrasound transducer housings 24 and delivery systems 12 can be used, preferably a delivery system 12 produced by Dornier Medical Systems, Inc. and sold commercially is used. The delivery system 12 can be reamed out to fit the size of ultrasound transducer housing assembly 30 as desired.

The ultrasound transducer housing assembly 30 can comprise a wide variety of configurations. Preferably, the assembly 30 is produced by producing apertures 31 in a thin walled tube 32, through which the power leads 34 for the ultrasound crystal 22 are run as shown in FIG. 14. The thin walled tube 32 can comprise a variety of biocompatible, noncorrosive materials, although preferably No. 304 stainless steel (thin needles stock) is used. The wires are run through the apertures 31, and an ultrasound crystal 22 is slid over the power leads 34, and soldered thereto. Any number of crystals 22 can be mounted this way, depending on the length of the thin wall tube 32 and the application desired. Next, silicone sealant 38 such as that sold commercially by General Electric as Silicon II Glue Seal and Gasket is deposited between the ultrasound crystals 22 and over the thin walled tube 32. The silicone sealant 38 acts as an adhesive, but allows the vibration necessary for efficient ultrasound energy radiation. The silicone sealant 38 also provides a water tight seal. While the assembly could be used in this form, preferably the assembly 30 is covered with shrink-wrap material 40 such as "SPIROBOUND" heat-shrink tubing which shrinks when exposed to heat. The shrink-wrap is exposed to a conventional heat source such as a propane torch in a controlled manner, and one obtains even shrinkage and a good seal by technique such as rotating the assembly 30 while heating. The resulting assembly is robust and highly efficient.

While a variety of ultrasound crystals 22 can be used, preferably the ultrasound crystal 22 shown in FIGS. 15A and 15B is used. For additional transducer details, please see FIGS. 14A and 14B. This ultrasound crystal 22 is preferably provided by Stavely Sensors, Inc. of East Hartford, Conn. Or Valpey-Fischer Corp of Hopkinton, Mass., and produces extremely high power output for a small sized transducer.

EXAMPLE

In accordance with this form of the invention, a transurethral multielement ultrasound applicator was used as a means of improving heating penetration, spatial localization, and dynamic control to afford better treatments for cancer and BPH. This structure provided longitudinal control of heating to cover the anterior-lateral portion of the prostate while sparing the region around the rectum and verumontanum. Computer simulations, acoustic measurements, and in vivo thermal dosimetry studies confirmed the usefulness of this form of the invention.

For a nonlimiting, illustrative example, prototype applicators were fabricated with four tubular transducer elements (each 6 mm long, 2.5 mm OD) attached to form a segmented array. Separation between elements was approximately 0.5 mm. Each transducer was modified to produce uniform coverage of the anterior and lateral portions of the prostate and to ensure that no acoustic energy would be delivered to the rectum during clinical use. The multielement applicator was designed to be inserted within a modified catheter delivery system previously developed for microwave BPH therapy (Dornier Medical Systems, Inc.), with annular counter-current flow for water coupling of the acoustic energy and temperature regulation of the catheter/urethra interface. (The cooling provided by the delivery system protects the urethra). The heating performance of these ultrasound applicator was evaluated using computer simulation programs to calculate the acoustic fields and corresponding thermal distributions in tissue. The power deposition (<q>) of these cylindrical sources in tissue can be approximated by the following expression:

$$<q> = \frac{2\alpha I_o f r_o}{r} e^{-2\alpha(r-r_o)} \quad (1)$$

where $I_0$ is the intensity at the transducer surface, $r_0$ is the radius of the transducer, r is the radial distance from the center of the transducer, $\alpha$ is the amplitude attenuation coefficient, and f is the frequence (MHz).

The temperature distributions resulting from the compiled power disposition patterns were calculated using the bio-heat transfer equation (BHTE), a descriptive model of tissue thermal characteristics:

$$\nabla 2(kT) - \alpha_b c_b (T - T_a) + <q> = 0 \quad (2)$$

where k is the tissue thermal conductivity, w is the blood perfusion rate, $c_b$ is the specific heat of tissue, T is the tissue temperature and $T_a$ is the arterial blood temperature. The steady-state solution to this equation was computed using the finite difference technique with successive over-relaxation. Typical values used were: $\alpha$=5 Np m$^{-1}$ MHz$^{-1}$, k=0.528 W m$^{-1}$ °C.$^{-1}$, w=1-10 kg m$^{-3}$ s$^{-1}$, c=3680 J kg$^{-1}$ °C.$^{-1}$, p=1000 kg m$^{-3}$. A perfusion of w=2.0 kg m$^{-3}$ s$^{-1}$ represents a moderately perfused tissue (resting muscle); most tumors range from 0.1-5.0 kg m$^{-3}$ s$^{-1}$. These simulations were configured to accurately model the presence of applicator water cooling of the applicator/tissue interface. The acoustic force-balance technique adapted for cylindrical radiators was used to measure the acoustic output power from these tubular transducers as a function of drive frequence and applied electrical power.

Figure 6:
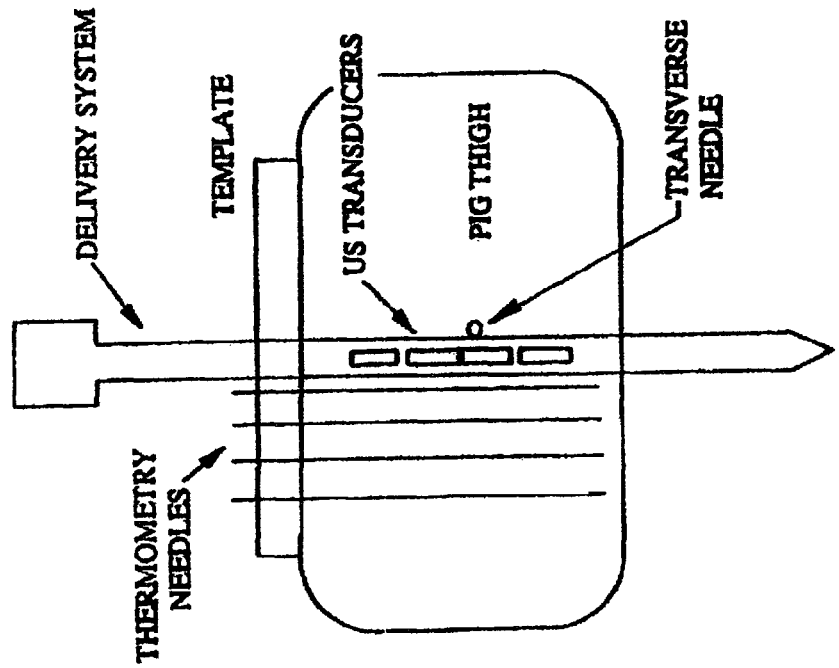
FIG. 6 illustrates a front view of the template implant for in vivo thermometry placement with respect to the applicator for thermal dosimetry measurements.
Figure 5:
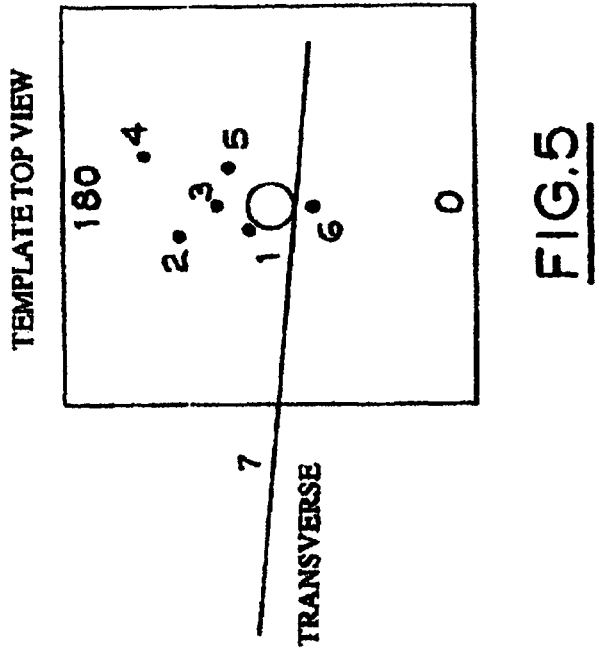
FIG. 5 shows a top view of the template implant for in vivo thermometry placement with respect to the applicator for thermal dosimetry measurements.

A 100 lb female farm pig was anesthetized using 1.5% Isoflourane and 0.6 l/min 02. A 0.5 inch thick Plexiglas template was used to ensure alignment of the thermometry probe tracks with the catheter delivery system (see FIGS. 5 and 6 for set up). 20 g. needles were inserted through the template for thermometry tracks at radial distances of 0.5 to 3.0 cm from the catheter wall but aligned with the axis of the delivery system. A tangential thermometry track was inserted orthogonal to the axis of the delivery system, 5 cm deep within the thigh, and glancing the surface of the catheter delivery system. Multijunction thermocouple probes were inserted within the needles and moved in 0.5 cm increments to obtain temperature maps along the length of the applicator. The approximate radial depth of sensed needles from the outer surface of the delivery catheter was 0.5, 1.0, 2.0 and 3.0 cm.

A multichannel RF amplifier system was used to power each transducer within the applicator. The frequency sweep on center frequency for each transducer was adjusted to produce a uniform pressure disturbance as visualized on the surface of water. A flow rate of 220 ml/min of 35° C. degassed water was maintained to the delivery system for the duration of the experiment.

The applicator was aligned within the catheter so that the "dead zone" aimed at #6 (probe track 6) and the central heating zone was aimed at #3. 2 watts of RF power was applied to each transducer element of the applicator until a pseudo steady-state was achieved after 5 minutes. Temperature maps were obtained for all thermometry probes, and then the power was turned off. The applicator was then rotated counter clockwise by 30° within the delivery system. After the tissue cooled back to equilibrium (10-20 min) the process was repeated. This sequence was repeated until the pseudo-steady-state temperature profiles were measured for each thermometry tract as the applicator was rotated in 30° increments for a total of 180°.

Figure 7:
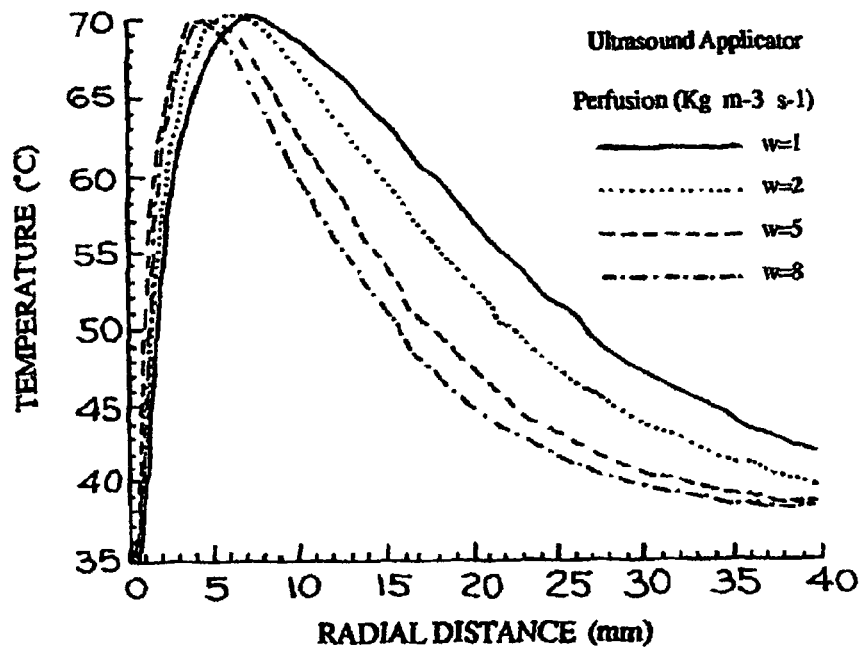
FIG. 7 illustrates simulated temperature profiles from a 2.5 mm diameter ultrasound applicator within a 6 mm diameter water-cooled delivery catheter with $T_c$ equal to 20° C.

Simulated radial temperature profiles (see FIG. 7) illustrated that effective heating is possible to 2 cm depth with concurrent cooling to protect the urethral mucosa ($T_c$=20° C., 7 MHz ultrasound). These experimental results (see FIG. 9) demonstrate the distinct advantage of multielement ultrasound applicators over other techniques: the power deposition along the applicator length can be adjusted to produce more desirable (elongated) temperature distributions such as adjusting heating length and accommodating dynamic changes in blood perfusion and tissue heterogeneity.

Figure 8:
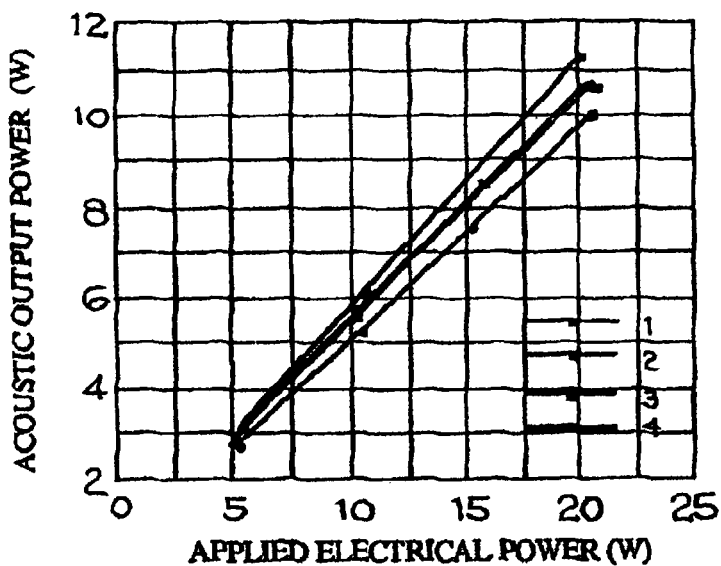
FIG. 8 illustrates acoustic output power levels as a function of electrical input power for four individual tubular array transducers driven at peak resonant frequency.
Figure 9A:
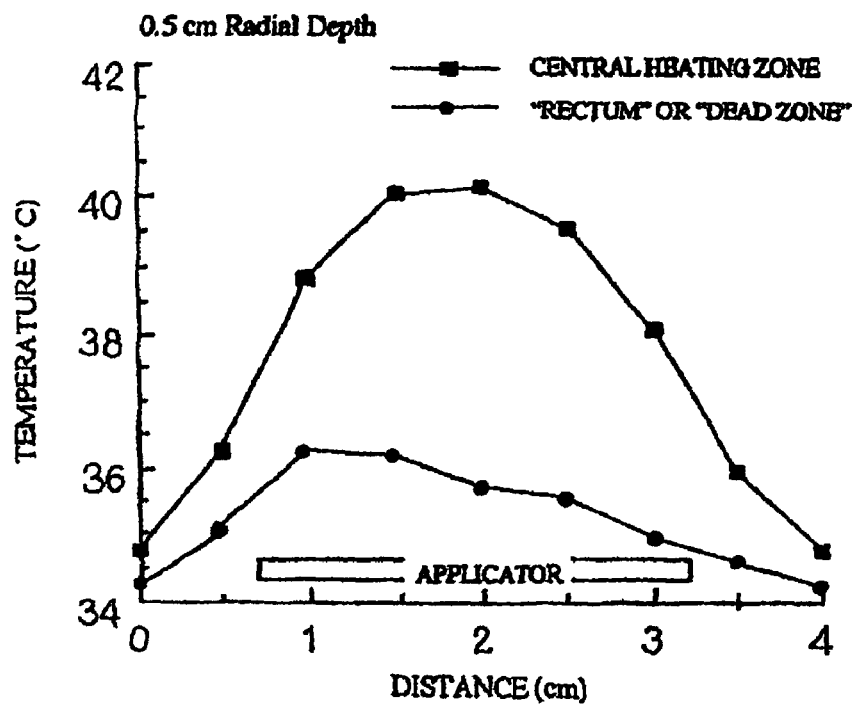
Figure 9B:
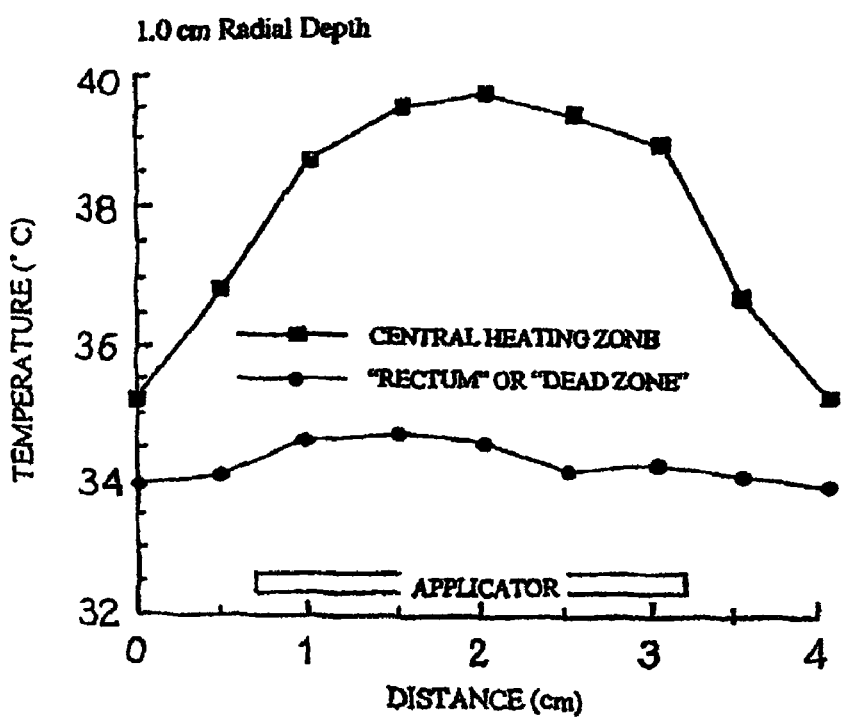
Figure 9C:
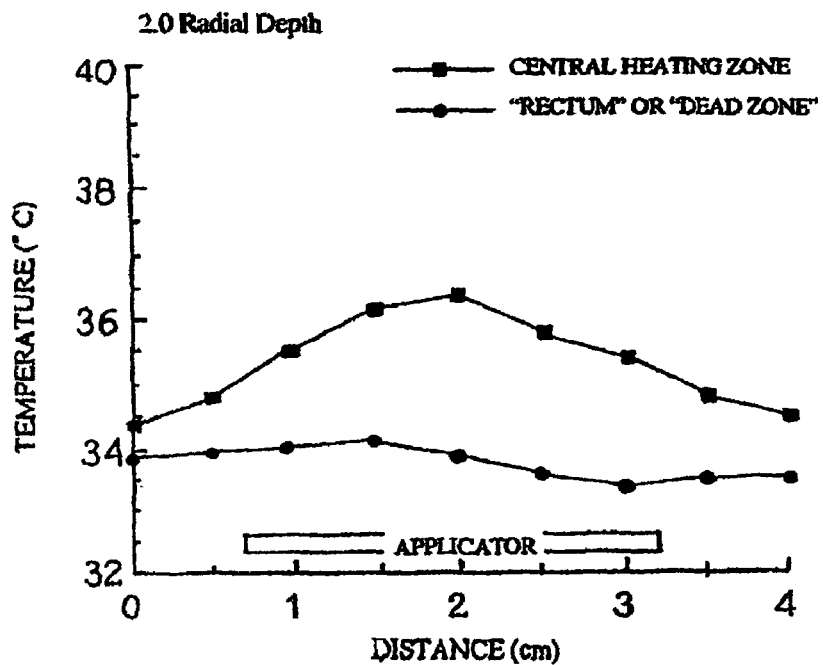
Figure 9D:
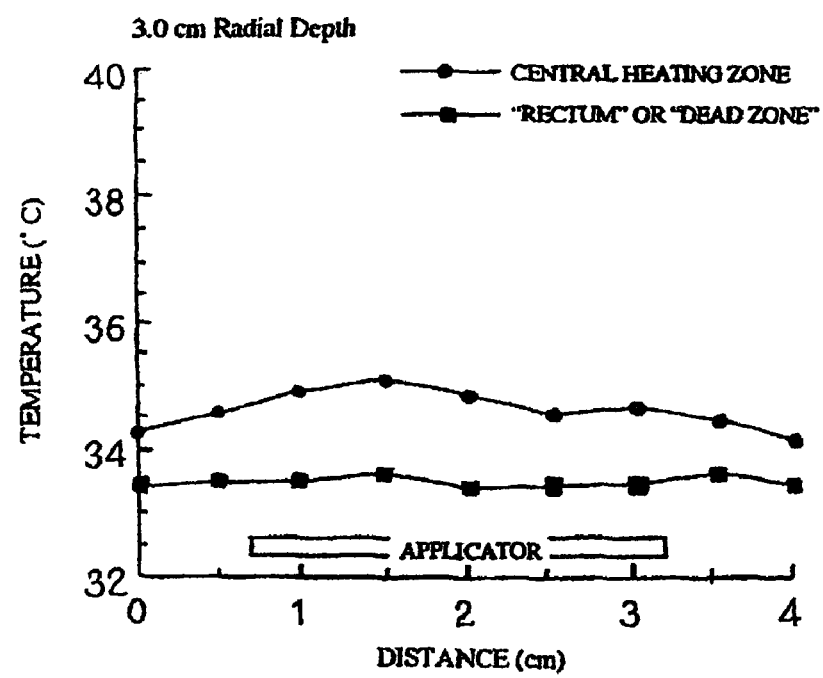

The acoustic efficiencies of these cylindrical ultrasound transducers was between 55-60% at the peak resonant frequency. These efficiencies are high for such very small crystals. FIG. 8 demonstrates that acoustic power levels of almost 12 w per transducer are attainable with this applicator design.

The temperature distributions produced by this applicator in pig thigh muscle were measured using low temperature repetitive heating trials. (This was necessary to ensure repeatability between heating sessions and to avoid thermal damage to the tissue). The longitudinal temperature profiles at varying radial depths from the applicator surface are shown in FIGS. 9A-E, demonstrating that within the central heating zone the therapeutic region extends towards the ends of the applicator and is fairly uniform, while isolated from the "rectal" region. The tangential profiles (FIG. 10) measured across the central heating zone illustrate a radial extension of the heated region 2-3 cm diameter. From a series of measurements at different rotational angles, the steady-state peak (longitudinal) temperature rise as a function of applicator rotational angle at varying depths are shown in FIGS. 11A-E, illustrating the preferential localization of the heating to the anterior and lateral regions while protecting the rectum (located at zero degrees on the plots). Further data relating to temperature rise as a function of alignment angle and longitudinal distance along the application are plotted in FIGS. 12A-E.

Finally, the applicator was repositioned to the initial startup orientation, and 8-10 acoustic watts of power was applied to each transducer in order to thermally ablate the "target" region an pseudo steady state temperatures were obtained. The radial temperature distribution achieved during the ablative sequence is shown in FIG. 12.

These results verified the usefulness of using the transurethral ultrasound applicator of present invention for thermal therapy of the prostate. Theses applicators, inserted within a water-cooled delivery-catheter, can produce heated regions extending more than 2 cm in radial depth, while sparing the urethral mucosa. A significant advantage of multi-transducer ultrasound applicators is that the longitudinal power deposition (heating pattern) can be dynamically altered in response to tissue heterogeneities, thermally induced changes in blood perfusion, and to tailor the size of the treated region. In addition, the beam distributions from these applicators can be shaped in order to produce desired circumferential or angular heating patterns which can protect the rectal mucosa while localizing the energy deposition to the anterior and lateral sections. This is a significant improvement over previous designs using single antenna microwave energy sources, which produce more elliptical or "football shaped" distributions which can not be adjusted. The in vivo thermal dosimetry experiments also show that therapeutic temperatures in excess of 80° C. can be obtained with the present invention.

While preferred embodiments have been illustrated and described, it should be understood that changes and modifications can be made therein without departing from the invention in its broad aspects. Various feature of the invention are defined in the following claims.

What is claimed is:

1. An apparatus for applying thermal therapy to a prostate gland, the apparatus comprising:
    a support tube having a longitudinal central passageway;
    a first ultrasound transducer disposed on at least a portion of the support tube to generate ultrasound energy for thermal therapy of the prostate gland; and
    a power lead coupled to the first ultrasound transducer;
    wherein the first ultrasound transducer is configured to direct the generated ultrasound energy to selectively treat a region of the prostate gland;
    wherein the first ultrasound transducer includes a first portion and a second portion, and wherein only the first portion delivers energy so that treatment is directed to a selected region of the prostate gland,
    wherein the first ultrasound transducer is scored such that power is only delivered to the first portion of the transducer.

2. An apparatus as recited in claim 1, wherein the transducer is cylindrical in shape; and
    wherein the scores run longitudinally along the length of the first ultrasound transducer, so that the first portion provides a specific radial direction for the delivery of ultrasound energy.

3. An apparatus as recited in claim 1, wherein the first ultrasound transducer is configured such that ultrasound energy is directed in an angular heating pattern.

4. An apparatus as recited in claim 3, wherein first ultrasound transducer is configured such that ultrasound energy is directed away from the rectum.

5. An apparatus as recited in claim 1, wherein the power lead is channeled through the central passageway.

6. An apparatus as recited in claim 1, wherein the first ultrasound transducer has a curvilinear cross-section to focus the generated ultrasound energy at the treatment region.

7. An apparatus as recited in claim 1, wherein the first ultrasound transducer comprises a cross-section having one or more planar surfaces.

8. An apparatus as recited in claim 1, further comprising a non-distensible balloon coupled to the transducer, the balloon configured to expand at a specific length to retain the transducer at the prostate gland.

9. An apparatus for applying thermal therapy to a prostate gland, the apparatus comprising:
    a support tube having a longitudinal central passageway;
    a first ultrasound transducer disposed on at least a portion of the support tube;
    a power lead coupled to the first ultrasound transducer to generate ultrasound energy for thermal therapy of the prostate gland; and
    means for directing the generated ultrasound energy to selectively treat a region of the prostate gland;
    wherein the first ultrasound transducer includes a first portion and a second portion, and wherein the means for directing the generated ultrasound energy further comprises means for activating only the first portion so that treatment is directed to a selected region of the prostate gland.

10. An apparatus as recited in claim 9, wherein the means for directing the generated ultrasound energy radially directs the ultrasound energy to create an angular heating pattern.

11. An apparatus as recited in claim 9, further comprising means for delivering a cooling fluid to the ultrasound applicator transducer to cool a non-target region of the patient.

12. An apparatus for applying thermal therapy to a prostate gland, the apparatus comprising:
    a support tube having a longitudinal central passageway;
    a first ultrasound transducer disposed on at least a portion of the support tube to generate ultrasound energy for thermal therapy of the prostate gland; and
    a power lead coupled to the first ultrasound transducer;
    wherein the first ultrasound transducer is configured to direct the generated ultrasound energy to selectively treat a region of the prostate gland;
    wherein the first ultrasound transducer includes a first portion and a second portion, and wherein only the first portion delivers energy so that treatment is directed to a selected region of the prostate gland; and
    an outer electrode surface surrounding the ultrasound transducer.

13. An apparatus as recited in claim 12, wherein a section of the outer electrode surface is removed to expose the first portion of the ultrasound transducer.

14. An apparatus as recited in claim 13, wherein the outer electrode surface is configured to radially direct the ultrasound energy to create an angular heating pattern.

15. An apparatus for applying thermal therapy to a prostate gland, the apparatus comprising:
    a support tube having a longitudinal central passageway;
    a first ultrasound transducer disposed on at least a portion of the support tube to generate ultrasound energy for thermal therapy of the prostate gland; and
    a power lead coupled to the first ultrasound transducer;
    wherein the first ultrasound transducer is configured to direct the generated ultrasound energy to selectively treat a region of the prostate gland; and
    a second ultrasound transducer adjacent to the first ultrasound transducer along the support member, the first and second ultrasound transducers being electrically isolated from each other, the second ultrasound transducer coupled to a second power lead such that the first and second ultrasound transducers may be powered independently.

16. An apparatus as recited in claim 15, further comprising a plurality ultrasound transducers adjacently disposed along the support member to form an array of transducers, each transducer individually coupled to a corresponding power lead such that the length and position of the ultrasound energy may be selectively controlled.

17. An apparatus as recited in claim 15, further comprising a sealant disposed between the first and second ultrasound transducers and the support tube.

18. An apparatus as recited in claim 15, wherein the first and second ultrasound transducers comprise cylindrical crystals concentrically disposed about the support tube.

19. An apparatus for applying thermal therapy to a prostate gland, the apparatus comprising:
    a support tube having a longitudinal central passageway;
    a first ultrasound transducer disposed on at least a portion of the support tube to generate ultrasound energy for thermal therapy of the prostate gland; and
    a power lead coupled to the first ultrasound transducer;
    wherein the first ultrasound transducer is configured to direct the generated ultrasound energy to selectively treat a region of the prostate gland; and
    an outer cover disposed over the first ultrasound transducer, and a fluid disposed between the transducer and the outer cover, the fluid providing efficient coupling of the ultrasound energy into the prostate gland.

20. An apparatus as recited in claim 19, further comprising means to cycle the fluid to selectively cool a non-target region of the patient.

21. An apparatus for applying thermal therapy to a prostate gland, the apparatus comprising:
   a support tube having a longitudinal central passageway;
   a first ultrasound transducer disposed on at least a portion of the support tube to generate ultrasound energy for thermal therapy of the prostate gland; and
   a power lead coupled to the first ultrasound transducer;
   wherein the first ultrasound transducer is configured to direct the generated ultrasound energy to selectively treat a region of the prostate gland;
   wherein the first ultrasound transducer includes a first portion and a second portion; and
   wherein the first portion and the second portion are individually powered so that either the first portion or the second portion provide specific radial direction for the delivery of ultrasound energy to a selected region of the prostate gland.

22. An apparatus as recited in claim 21, wherein the first portion and the second portion are individually powered to provide dynamic control of the radial energy delivery.

23. An apparatus for applying thermal therapy to a prostate gland, the apparatus comprising:
   a support tube having a longitudinal central passageway;
   a first ultrasound transducer disposed on at least a portion of the support tube;
   a power lead coupled to the first ultrasound transducer to generate ultrasound energy for thermal therapy of the prostate gland;
   means for directing the generated ultrasound energy to selectively treat a region of the prostate gland;
   wherein the first ultrasound transducer comprises an outer electrode surface; and
   wherein the means for directing the generated ultrasound energy comprises removing a section of the outer electrode surface to form the second portion of the ultrasound transducer.

24. An apparatus as recited in claim 23, wherein the means for directing the generated ultrasound energy directs the heating pattern away from the rectum.

25. An apparatus for applying thermal therapy to a prostate gland, the apparatus comprising:
   a support tube having a longitudinal central passageway;
   a first ultrasound transducer disposed on at least a portion of the support tube;
   a power lead coupled to the first ultrasound transducer to generate ultrasound energy for thermal therapy of the prostate gland;
   means for directing the generated ultrasound energy to selectively treat a region of the prostate gland; and
   a second ultrasound transducer, and a means for controlling delivery of energy between the first and second ultrasound transducers to control the longitudinal extent of the ultrasound energy distribution.

* * * * *